United States Patent
Burwinkel et al.

(10) Patent No.: US 12,288,352 B2
(45) Date of Patent: Apr. 29, 2025

(54) MACHINE-LEARNING BASED IOL POSITION DETERMINATION

(71) Applicant: Carl Zeiss Meditec AG, Jena (DE)

(72) Inventors: Hendrik Burwinkel, Munich (DE); Holger Matz, Unterschneidheim (DE); Stefan Saur, Aalen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 294 days.

(21) Appl. No.: 17/759,350

(22) PCT Filed: Jan. 21, 2021

(86) PCT No.: PCT/EP2021/051296
§ 371 (c)(1),
(2) Date: Jul. 22, 2022

(87) PCT Pub. No.: WO2021/148515
PCT Pub. Date: Jul. 29, 2021

(65) Prior Publication Data
US 2023/0057686 A1    Feb. 23, 2023

(30) Foreign Application Priority Data
Jan. 24, 2020  (DE) .......................... 102020101761.8

(51) Int. Cl.
*G06K 9/00*  (2022.01)
*G06N 3/08*  (2023.01)
(Continued)

(52) U.S. Cl.
CPC ................. *G06T 7/70* (2017.01); *G06N 3/08* (2013.01); *G06T 7/0016* (2013.01); *G16H 30/40* (2018.01);
(Continued)

(58) Field of Classification Search
CPC .................... G06T 7/70; G06T 7/0016; G06T 2207/10101; G06T 2207/10132;
(Continued)

(56) References Cited

U.S. PATENT DOCUMENTS

2020/0015894 A1*  1/2020  Bor ....................... G06T 7/0012

FOREIGN PATENT DOCUMENTS

| DE | 102015225759 A1 |   | 6/2017 |           |
|----|-----------------|---|--------|-----------|
| EP | 2796087 A1      | * | 10/2014| A61B 3/0025 |
| EP | 2891452 A1      |   | 7/2015 |           |
| EP | 3491996 A1      |   | 6/2019 |           |

OTHER PUBLICATIONS

Nov. 23, 2020 Office Action issued in corresponding German Application No. 10 2020 101 761.8 (in German language).
(Continued)

*Primary Examiner* — Xin Jia
(74) *Attorney, Agent, or Firm* — Honigman LLP; Brett A. Krueger (57) ABSTRACT

The invention relates to a computer-assisted method for position determination for an intraocular lens supported by machine learning. The method comprises providing a scan result for an eye. The scan result here represents an image of an anatomical structure of the eye. The method further comprises use of a trained machine learning system for the direct determination of a final location of an intraocular lens to be fitted, wherein digital data of the scan of the eye is used as the input data for the machine learning system.

29 Claims, 7 Drawing Sheets

(51) Int. Cl.
  *G06T 7/00* (2017.01)
  *G06T 7/70* (2017.01)
  *G16H 30/40* (2018.01)
(52) U.S. Cl.
  CPC .............. *G06T 2207/10101* (2013.01); *G06T 2207/10132* (2013.01); *G06T 2207/20081* (2013.01); *G06T 2207/20084* (2013.01); *G06T 2207/30041* (2013.01); *G06T 2207/30052* (2013.01)
(58) Field of Classification Search
  CPC .......... G06T 2207/20081; G06T 2207/20084; G06T 2207/30041; G06T 2207/30052; G06N 3/08; G06N 3/045; G06N 3/044; G16H 30/40; G16H 50/70; A61B 8/085; A61B 3/1005; A61B 3/102; A61B 3/112; A61B 8/10; A61B 8/5223
  See application file for complete search history.

(56) References Cited

OTHER PUBLICATIONS

Graph neural networks: Variations and applications, Alexander Gaunt, University of Cambridge, Mar. 15, 2018, URL: https://www.microsoft.com/en-us/research/video/graph-neural-networks-variations-applications/.
May 3, 2021 Written Opinion (WO) of the International Searching Authority (ISA) and International Search Report (ISR) issued in International Application No. PCT/EP2021/051296 (with English Translation).
Tianle Ma et al: "Incorporating Biological Knowledge with Factor Graph Neural Network for Interpretable Deep Learning", arxiv.org, Cornell University Library, 201 Olin Library Cornell University Ithaca, NY 14853, 3. Jun. 2019 (Jun. 3, 2019), XP081372034, Zusammenfassung.

* cited by examiner

MACHINE-LEARNING BASED IOL POSITION DETERMINATION

CROSS REFERENCE TO RELATED APPLICATIONS

This application is the U.S. national stage of PCT/EP2021/051296 filed on Jan. 21, 2021, which claims priority of German Patent Application DE 10 2020 101 761.8 filed on Jan. 24, 2020. The disclosures of these prior applications are considered part of the disclosure of this application and are hereby incorporated by reference in their entireties.

TECHNICAL FIELD

The disclosure relates to a determination of position of an intraocular lens and, in particular, to a machine learning-supported post-operative determination of position for an intraocular lens, to a corresponding system and to a corresponding computer program product

BACKGROUND

Replacing the biological lens of an eye with an artificial intraocular lens—for example, in the case of an (age-related) refractive error or in the case of cataracts—has become ever more common in the field of ophthalmology in recent years. In the process, the biological lens is detached from the capsular bag by way of a minimally invasive intervention and removed. The lens, which has become opacified in the case of a cataract, is then replaced by an artificial lens implant. In the process, this artificial lens implant or intraocular lens is inserted into the then empty capsular bag. However, the intraocular lens is typically significantly smaller than the original biological lens, and so it has a certain amount of leeway within the capsular bag. On the sides of the intraocular lens there usually are special protrusions that should ensure that the intraocular lens is anchored at a fixed position within the capsular bag over time. What can regularly be observed in the process is that the position of the lens slowly approaches a final position during an entry process which may extend over several weeks. This position typically deviates from the position of the lens directly following the operation. However, it is essential for an optimal operation result to know a possible final position and orientation of the intraocular lens within the eye in order to match the refractive power of the lens to fit the ultimate, final position of the lens in the eye, which sets in weeks later.

This is also a difficult undertaking since, inter alia, the capsular bag, which is held within the eye by way of surrounding tissue (muscles and tendons 208), changes its shape during the growing-in process.

It has been conventional up until now to carry out a manual extraction of geometric properties of the patients eye from the OCT (optical coherence tomography) image data presurgery, the geometric data extracted including, for example, axial length, anterior chamber depth or lens thickness. The extracted information of the OCT images obtained thus is therefore restricted to only a few predefined geometric variables. As a result, a large proportion of possibly important information actually present in the recorded digital images is lost to a good intraocular lens (IOL) position prediction.

Based on the disadvantages of the known methods for manually extracting geometric properties of the patients eye, an underlying object of the concept presented here consists of predicting a direct IOL position prediction for an intraocular lens following a growing-in phase.

SUMMARY

This object is achieved by means of the method proposed here, the corresponding system and the associated computer program product in accordance with the independent claims. Further embodiments are described by the respective dependent claims.

According to an aspect of the present disclosure, a computer-implemented method for a machine learning-supported determination of position for an intraocular lens is presented. The method includes a provision of a scan result of an eye. The scan result represents an image of an anatomical structure of the eye. Furthermore, the method includes using a trained machine learning system to directly determine a final location of an intraocular lens to be inserted. In this case, digital data of the scan of the eye serve as input data for the machine learning system.

According to another aspect of the present disclosure, a corresponding prediction system for a machine learning-supported determination of position for an intraocular lens is presented. In this case, the prediction system comprises: a provision module which is adapted to provide a scan result of an eye. In this case, the scan result represents an image of an anatomical structure of the eye. Moreover, the system comprises a trained machine learning system adapted to directly determine a final location of an intraocular lens to be inserted, digital data of the scan of the eye serving as input data for the machine learning system.

Furthermore, embodiments can relate to a computer program product able to be accessed from a computer-usable or computer-readable medium that comprises program code for use by, or in conjunction with, a computer or other instruction processing systems. In the context of this description, a computer-usable or computer-readable medium can be any device that is suitable for storing, communicating, transferring, or transporting the program code.

The computer-implemented method for a machine learning-supported determination of position for an intraocular lens has a plurality of advantages and technical effects which may also apply accordingly to the associated system. The proposed method provides prediction of a direct determination of position in respect of a final position and orientation of an intraocular lens following a relatively long growing-in phase. Previous methods essentially use manual determination methods for certain eye parameters. These can then possibly be used for further image processing methods in order to determine a position and orientation of an inserted (post-surgery) intraocular lens. However, this results in a media disruption when processing the scan results, for example of OCT equipment, in order firstly to determine geometric parameters of the eye in more or less manual fashion and secondly, in a subsequent step, to undertake a determination of position for the intraocular lens.

The method presented here avoids this media disruption by virtue of initially determining biological parameters of the eye by way of a DNN (deep neural network) in the form of a CNN (convolutional neural network) and subsequently supplying the biological parameters determined thus, but also the scan results, to a graph-based neural network.

In this case, the graph contains already annotated images (annotated with biometric data and the final location of the intraocular lens) of previous operations, and the information from the new scan results of one or more digital images is processed by means of the graph-based neural network. In this way, the graph-based neural network has available all available digital image information in addition to geometric parameters of the eye to be operated on. In this way, potentially available information is not dispensed with anywhere. Hence, complete or OCT image information can be used directly and immediately for an IOL position prediction. Hence, a pre-extraction of geometric variables of the eye has been made redundant.

This significantly increases the prediction speed and potential sources of error are reduced. Since training of the graph-based neural network can be undertaken using clinic-specific digital images, it is also possible to consider clinic-specific peculiarities when training the neural network, and hence allow these to be taken into account for the predictions of the final IOL position prediction.

Furthermore, the method proposed here also allows the use of a sequence of digital images. In the process, it is possible to directly take account of the accommodation of the eye when the crystalline lens is still situated within the eye. In this way, it is possible to take account of additional information when determining the final IOL position and orientation in a grown-in state since available tendon and muscle behavior in and around the eye are able to be considered by way of the dynamic data.

Further exemplary embodiments are presented below, which have validity both in association with the method and in association with the corresponding system.

According to an advantageous embodiment of the disclosure, the scan of the eye may represent a sectional image of a plane within the eye, the smallest angle of the plane with the ocular axis—in particular within the eye—from the cornea to the retina being smaller than a specified maximum angle. Hence, the image plane extends substantially parallel (e.g., 10°) to the axis. Typically, the small angle would be less than 10°. However, the angle may also be up to 90° in a certain embodiment—in particular in the case of an en-face recording.

According to another exemplary embodiment of the method, the plane of the sectional image can be completely flat, or else it can be curved in another exemplary embodiment. The curvature can be symmetrical with respect to a predefined sectional plane of the eye. However, this may also be a curved free-form surface in a further exemplary embodiment. Hence, very different recording methods can be used to generate the sectional image.

In an extended exemplary embodiment of the method, the scan result may represent a plurality of images of the anatomical structure of the eye. Hence, there are options of a 3-D (3-dimensional) or else a 4-D (4-dimensional, corresponding to 3-D with an additional time component) representation of one or more sectional images of the eye. In particular, a 4-D representation facilitates a detection of changes over time, for example the accommodation of the eye.

In a special exemplary embodiment of the method, the scan of the eye can be carried out by means of optical coherence tomography (OCT). By way of example, use can be made of what are known as A-scans, B-scans, volume scans, or else a 4-D OCT method. Moreover, an ultrasound system can be used to generate a scan recording of the eye, in order to generate the scan in this way.

According to a further advantageous exemplary embodiment of the method, the latter additionally includes training the machine learning system with annotated scan results as input data for the machine learning system. In this case, a model can be generated in the machine learning system, said model rendering the final location of the intraocular lens inferable—or "predictable" in accordance with the terminology generally used in the field of machine learning. One element of this aspect of the method consists of the OCT scanning data or images or recordings being made prior to a corresponding operation while the annotations are implemented following an operation—in particular following a fully completed growing-in phase for an intraocular lens. This allows a link between preoperative image data and postoperative, actual position and orientation coordinates of the intraocular lens to be established in the machine learning system.

According to a further advantageous exemplary embodiment of the method, parameters of the eye extracted from the scan result can be used as additional input data for training the machine learning system. Individual items of the following list, or combinations thereof, can be specified as typical parameters of the eye: axial length, anterior chamber depth, lens thickness, posterior chamber depth, corneal thickness, corneal keratometry, lens equatorial plane, white-to-white distance and pupil size.

According to a representative exemplary embodiment of the method, the machine learning system can be a neural network, in particular a deep neural network (CNN=convolutional deep neural network). Such neural networks are particularly suitable for processing digital images, such as the scan results of the eye.

In a developed exemplary embodiment of the method, the use of the trained machine learning system may include integrating the scan result of the eye into a graph of available annotated eye recordings of the same type—for example a B-scan. In this case, moreover, the integration into the graph can be undertaken on the basis of biometric data (one example would be the axial length of the eye, or else many further determined parameters of the eye) of the scan result of the eye. What is advantageous here is that the scan results of the eye—i.e., substantially the associated digital image—are linked to the determined parameters of the eye—i.e., annotated. As a result of a comparison of the parameters of the eye determined thus with the corresponding parameters of the already available images of the graph, the newly added image can be elegantly inserted into the graph.

According to a corresponding exemplary embodiment, the graph can therefore be constructed according to the nearest neighbor principle. In this case, images for which for example only a single parameter is present can be arranged in the graph structure in such a way that digital images whose parameter values lie closest together in comparison with other digital images are represented as direct neighbors in the graph.

According to a viable exemplary embodiment of the method, the trained machine learning system can have two stages. In this case, the first stage can have a first machine learning system—for example a CNN—which comprises a trained model, by means of which biometric data of the eye are predictable. Moreover, this exemplary embodiment can have the second stage in the machine learning system. This second stage can comprise a trained model which uses the biometric data predicted by the first machine learning system and the graph—including the scan of the eye available there or the other digital recordings including the respectively associated annotation—as input data in order to predict the final location of the intraocular lens to be inserted.

The second stage can be a special form of a machine learning system, for example a GAT (graph attention network), a GCN (graph convolutional network) or a Graph-Sage system. That is to say, the method proposed here does not rely on only one type of machine learning system. Rather, depending on the type and structure of the graph used and the other available data, different machine learning systems can be used for processing graph data.

In accordance therewith and in accordance with a further exemplary embodiment, further parameters of an eye patient can also be used as input data for the second machine learning system. These further parameters can be selected from the group consisting of age, sex, operation location, operating physician, operation method, and extended pathology data. In the process, a possible preliminary treatment of the eye, into which the intraocular lens is to be inserted, can also be taken into account. Moreover, it turns out that the operation location parameter renders special clinic-specific or physician-specific parameters capturable, which parameters would not be usable, or only usable with great outlay, for the prediction of the post-operative position of the intraocular lens by way of other methods.

Further exemplary embodiments relate to the type or the production method for the scan results provided. The scan results can be an A-scan, a B-scan, en-face scan data and/or dynamic eye data. Hence scan results produced with different equipment or different methods are usable for the method proposed here.

According to a developed exemplary embodiment of the method, a recurrent neural network (RNN) can be used to detect a change of the eye over time in the case of dynamic eye data. Hence, the accommodation of the eye, for example, can be used as additional parameter or biological parameter of the eye for the aforementioned machine learning system.

It should be pointed out that exemplary embodiments of the disclosure may be described with reference to different implementation categories. In particular, some exemplary embodiments are described with reference to a method, whereas other exemplary embodiments may be described in the context of corresponding devices. Regardless of this, it is possible for a person skilled in the art to identify and to combine possible combinations of the features of the method and also possible combinations of features with the corresponding system from the description above and below—if not specified otherwise—even if these belong to different claim categories.

Aspects already described above and additional aspects of the present disclosure become apparent inter alia from the exemplary embodiments that are described and from the additional further specific embodiments described with reference to the figures.

BRIEF DESCRIPTION OF THE DRAWINGS

Preferred exemplary embodiments of the present disclosure are described by way of example and with reference to the following figures.

DETAILED DESCRIPTION PREFERRED EMBODIMENTS

In the context of this description, conventions, terms and/or expressions should be understood as follows:

The term "machine learning-supported determination of position" determines a determination of position and orientation for an intraocular lens which is inserted into the eye in place of the crystalline lens. To enable optimal vision for the patient, it is necessary to have optimal matching of the refractive power of the lens to the position and orientation of the lens within the eye. By way of example, a higher refractive power would be required should the lens be located closer to the retina after the operation. The difficulty in such operations consists in predicting where the intraocular lens will in fact be located in the eye following a relatively long growing-in process which may take several weeks. The method presented here, which is supported or carried out by one or more machine learning systems evaluates OCT data in order to carry out a direct and immediate determination of IOL position, which is ascertained in an integrated process.

The term "intraocular lens" describes an artificial lens which is inserted into the eye of a patient by surgery to replace the natural, biological lens.

The term "scan result" describes digital data which represent the result of an OCT examination on an eye of a patient.

The term "optical coherence tomography" (abbreviated OCT) describes a known imaging method of ophthalmology, for obtaining 2- and 3-dimensional recordings of scattering materials (e.g., biological tissue) with micrometer resolution. In the process, use is essentially made of a light source, a beam splitter and a sensor—for example in the form of a digital image sensor. In ophthalmology, OCT is used to detect spatial differences in the reflection behavior of individual retinal layers, and morphological structures are represented with a high resolution.

The term "annotated scan result" describes image data which were augmented with additional information. In the context of the text present here, these are essentially digital image data—in particular scan results—which were augmented by determined parameter values of the eye (i.e., metadata).

The term "anatomical structure" describes the actually present physical conditions of a biological unit, in particular an eye in this case.

The term "machine learning system" describes a system that is also typically assigned to a method, said system learning from examples. To this end, annotated training data is fed to the machine learning system in order to predict output values—output classes in the case of a classification system—that were already set in advance. If the output classes are correctly output with sufficient precision—i.e., an error rate determined in advance—the machine learning system is referred to as trained. Several machine learning systems are known. These include neural networks, convolutional neural networks (CNN) or else recurrent neural networks (RNN).

In principle, the term "machine learning" is a basic term or a basic function of artificial intelligence, wherein statistical methods, for example, are used to give computer systems the ability to "learn". By way of example, certain behavioral patterns within a specific task range are optimized in this case. The methods that are used give trained machine learning systems the ability to analyze data without requiring explicit procedural programming for this purpose. Typically, an NN (neural network) or CNN (convolutional neural network) is an example of a system for machine learning, for forming a network of nodes which act as artificial neurons, and artificial connections between the artificial neurons—so-called links—, wherein parameters—e.g., weight parameters for the links—can be assigned to the artificial links. When training the neural network, the weight parameter values of the links adjust automatically on the basis of input signals so as to generate a desired result. In the case of supervised learning, the images supplied as input values (training data)—generally (input) data—are supplemented with desired output data (annotations) in order to display a desired output value (desired class). Considered very generally, mapping of input data onto output data is learned.

The term "neural network" describes a network made of electronically realized nodes with one or more inputs and one or more outputs for carrying out calculation operations. Here, selected nodes are interconnected by means of connections—so-called links or edges. The connections can have certain attributes, for example weighting parameter values, by means of which output values of preceding nodes can be influenced.

Neural networks are typically constructed in a plurality of layers. At least an input layer, a hidden layer, and an output layer are present. In a simple example, image data can be supplied to the input layer and the output layer can have classification results in respect of the image data. However, typical neural networks have a large number of hidden layers. The way in which the nodes are connected by links depends on the type of the respective neural network.

The term "direct determination", in particular "direct determination of a final location", of an IOL in this case means that a determination of the IOL position is carried out directly and without detours and without manual intermediate steps, proceeding from scan results of an eye. In this case, the result of the determination of the IOL position relates to the position and orientation of a grown-in IOL following a relatively long growing-in phase, which is assumed to have been completed so that a further displacement of the intraocular lens is no longer expected. The direct determination characterizes a direct advantage over known methods, in which manual intermediate steps are required to recognize and determine parameter values of the eye.

The term "parameter value" describes geometric or biometric values of an eye of a patient. Examples of parameter values of an eye are discussed in more detail on the basis of FIG. 3.

The "nearest neighbor principle" describes a form of a search on the basis of a distance specification of entities. Ultimately, this relates to an optimization problem for finding a point which is closest to another data point in a given data set. In this case, the proximity is frequently expressed by a similarity function. In this case, objects that are less similar have greater function values. The determination of similarity is often based on a distance metric. In this case, the similarity is determined by the Euclidean distance, the Manhattan distance, or any other distance metric.

The term "A-scan" (also referred to as axial depth scan) describes a one-dimensional result of a scan of a patient's eye, which provides information about geometric dimensions and locations of structures within the eye.

The term "B-scan" describes a lateral overlay of a plurality of the aforementioned A-scans, to obtain a section through the eye. Volume views are also generable by combining a plurality of layers of the eye generated thus.

The term "en face OCT" in this case describes a method for producing transverse sectional images of the eye—in contrast to longitudinal sectional images using the aforementioned A- or B-scans.

The term "dynamic eye data" describes a sequence of simple sectional images of the eye—usually in the same position—in order to recognize dynamic changes, that is to say changes over time.

The term "GAT" (graph attention network) describes a neural network operating on graph-structured data. It exhibits a better behavior than the older "graphical convolutional networks" (GCNs). In the process, use is made of masked self-referenced layers of nodes which improve the known approximations in CGNs without building on computationally intensive matrix operations.

The term "GCN" (graphical convolutional network) describes a certain architecture of neural networks which can operate directly on graphs and can use the structural information present there.

The term "GraphSage" describes a framework for inductive representation learning in the context of large graphs. In this case, GraphSage can be used to generate low-dimensional vector representations for nodes and it is particularly useful for diagrams with comprehensive node attribute information.

The term "recurrent neural network" denotes neural networks which, in contrast to the feedforward networks, are distinguished by links of neurons (i.e., nodes) of one layer to neurons of the same or a preceding layer. This is the preferred manner of interconnection of neural networks in the brain, in particular in the neocortex. In artificial neural networks, recurrent connections of model neurons are used to discover time-encoded—i.e., dynamic—information in the data. Examples of such recurrent neural networks include the Elman network, the Jordan network, the Hopfield network and the fully connected neural network. They are also suitable for examining a dynamic behavior in recordings of eyes, in particular for taking account of the accommodation behavior of the eye.

The term "digital image"—e.g., a scan—in this case describes an image representation of, or the result of generating an amount of data in the form of pixel data from, a physically existing article: by way of example, a retina of an eye in this case. More generally, a "digital image" can be understood to be a two-dimensional signal matrix. The individual vectors of the matrix can be adjoined to one another in order thus to generate an input vector for a layer of a CNN. The digital images can also be individual frames of video sequences.

The term "convolutional neural network" (CNN)—as one example of a classifier/classifier system—describes a class of artificial neural networks that are based on feedforward techniques. They are often used for image analysis using images or the pixels thereof as input data. The main components of convolutional neural networks are in this case convolution layers (hence the name) that allow efficient evaluation through parameter sharing. In contrast to the CNN, each pixel of the recorded image would typically be associated with an artificial neuron of the neural network as an input value in a conventional neural network.

Mention is also made of the fact that deep neural networks (DNN) consist of a plurality of layers having different functions—for example an input layer, an output layer and a plurality of interposed layers, for example for convolution operations, applying non-linear functions, dimension reduction, normalization functions, etc. The functions may be "executed in software" or special hardware assemblies may take over the calculation of the respective function values. The nodes can then consist of a memory for weight parameters and one or more signal amplifiers. Combinations of hardware and software elements are also usable.

Figure 1:
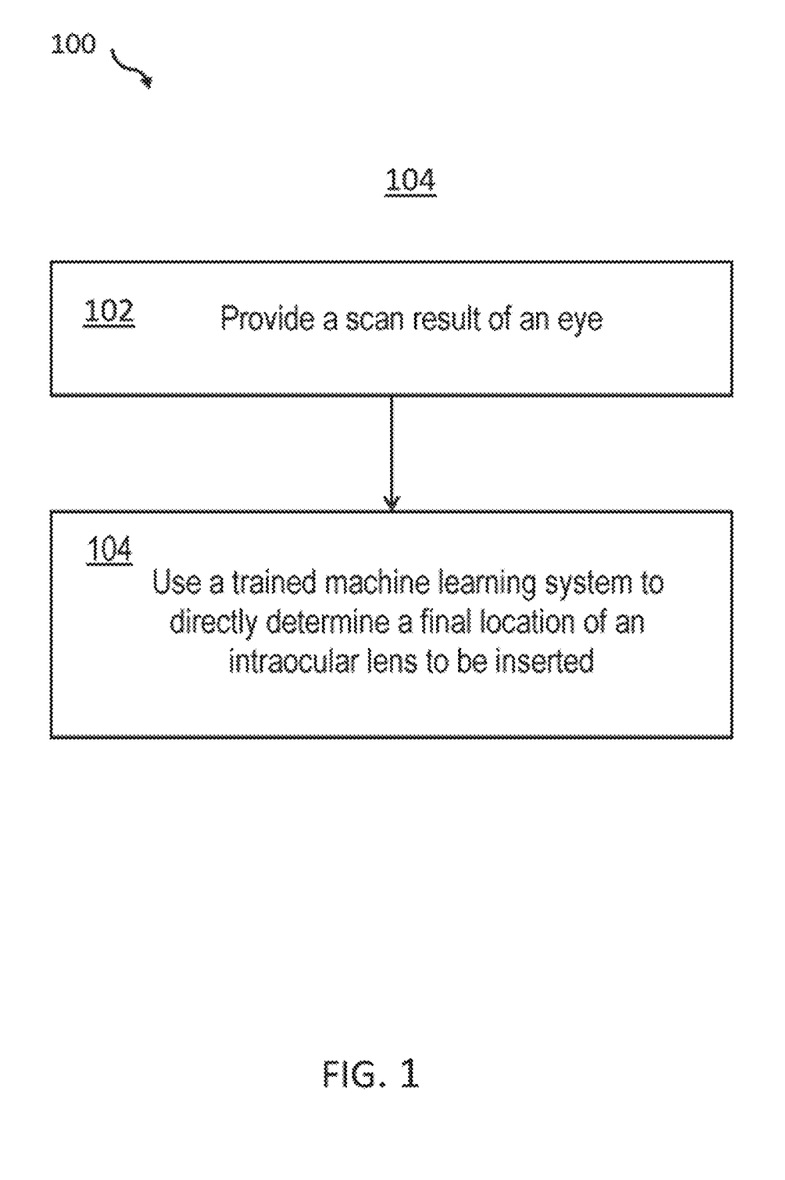
FIG. 1 illustrates a flowchart-like representation of an exemplary embodiment of the computer-implemented method according to the disclosure for a machine learning-supported determination of position for an intraocular lens.

A detailed description of the figures is given below. It is understood in this case that all of the details and information in the figures are illustrated schematically. Initially, a block diagram of an exemplary embodiment of the computer-implemented method according to the disclosure for a machine learning-supported determination of position for an intraocular lens is illustrated. Further exemplary embodiments or exemplary embodiments for the corresponding system are described below:

FIG. 1 illustrates a flowchart-like representation of an exemplary embodiment of the computer-implemented method 100 according to the disclosure for a machine learning-supported determination of position for an intraocular lens. The method includes providing 102 a scan result of an eye, that is to say a digital recording of an eye to be operated on. The scan result is an image of an anatomical structure of the eye. Furthermore, the method 100 includes using 104 a trained machine learning system to directly determine a final location of an intraocular lens to be inserted, digital data of the scan of the eye serving as input data for the machine learning system.

Reference is once again made to the fact that the method proposed here is a method for direct prediction of the final position and orientation—i.e., post-operative position and orientation following a growing-in phase—of the inserted intraocular lens. An intermediate step, which is almost always manual, for the determination of eye parameters then used for the prediction of position and orientation can be dispensed with. Moreover, the method is designed to predict the position and orientation after the growing-in phase of several weeks, and is therefore distinguished from other methods which possibly can predict a position directly after the operation.

Figure 2:
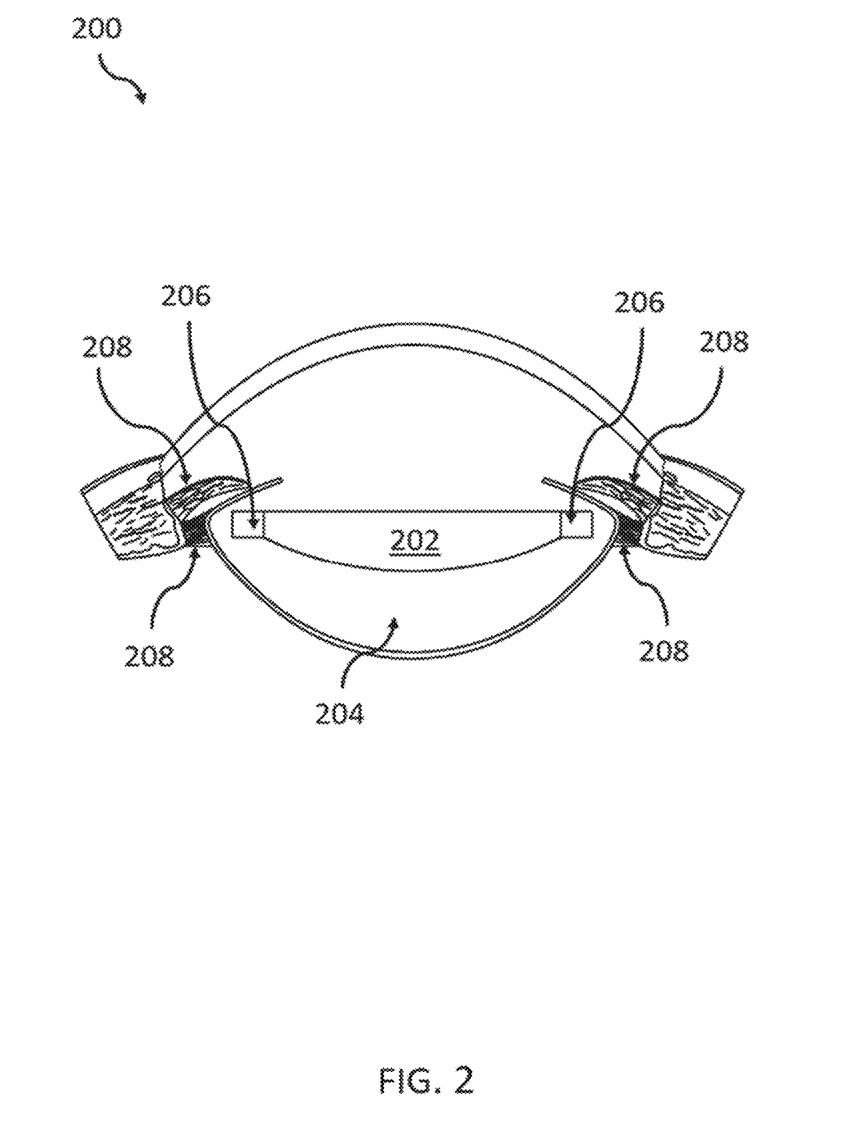
FIG. 2 depicts a cross section of a part of an eye.

FIG. 2 shows a symbolic representation of a cross section of an eye 200. It is possible to identify the inserted intraocular lens 202, which was operatively inserted into the capsular bag 204 following the removal of the natural crystalline lens. Lateral structures 206 on the intraocular lens 202 should ensure that the intraocular lens 202 is anchored truly stably in the capsular bag 204. However, a precise position of the intraocular lens 202 which sets in after a relatively long introduction phase of several weeks, for example, could practically not be predicted to date. This is due to the fact that, inter alia, the capsular bag 204 is substantially larger than the inserted intraocular lens 202 as it previously enclosed the entire natural but now removed crystalline lens. These tendons and muscular tissue, which anchor the capsular bag 204 in the eye or on the skull, change after such an operation, as a result of which the size, the shape, and the position and orientation of the capsular bag 204, and hence also the position and orientation of the inserted intraocular lens 202, also change. Hence there is also change in the distance between the inserted intraocular lens 202 and the retina situated further back in the eye. However, optimal postoperative results can only be achieved by optimal matching of the refractive power (refractive index) of the inserted intraocular lens 202 and the distance to the retina. Since the refractive power of the inserted intraocular lens 202 is normally not subsequently changeable, a prediction of the position and orientation of the inserted intraocular lens 202 is very desirable.

Figure 3:
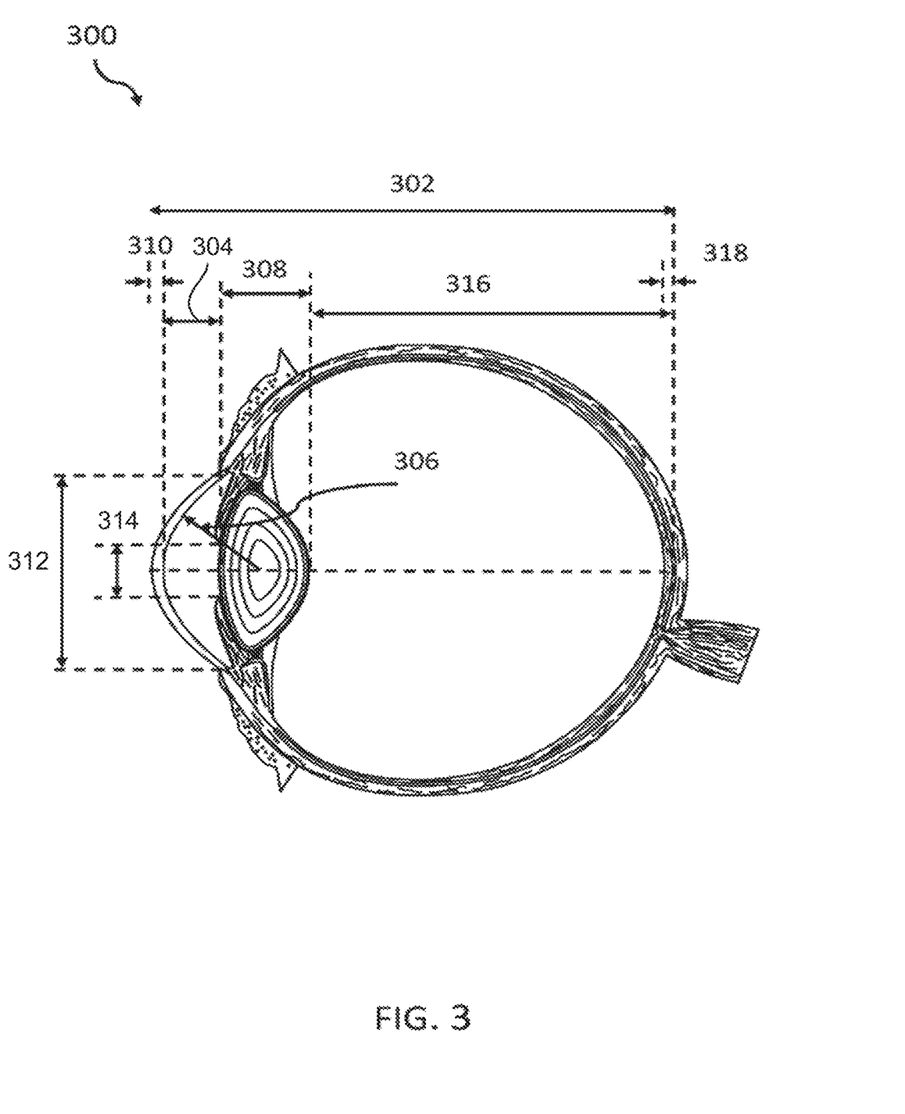
FIG. 3 illustrates an eye with different biometric parameters of the eye.

FIG. 3 depicts an eye 300 with different biometric parameters of the eye. In particular, the following parameters are represented: axial length 302 (AL), anterior chamber depth 304 (ACD), keratometry value 306 (K, radius), refractive power of the lens, lens thickness 308 (LT), central cornea thickness 310 (CCT), white-to-white distance 312 (WTW), pupil size 314 (PS), posterior chamber depth 316 (PCD), retina thickness 318 (RT).

Figure 4:
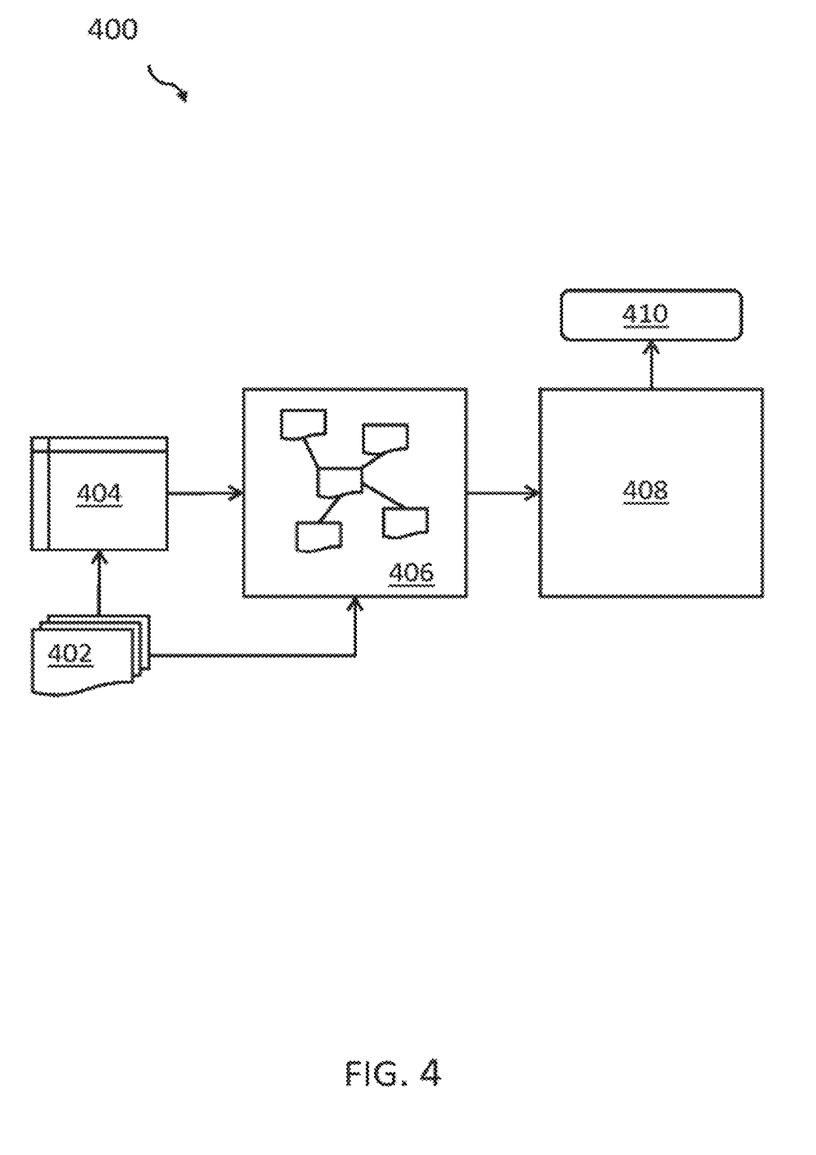
FIG. 4 illustrates a schematic structure of essential functional blocks of the underlying proposed method.

FIG. 4 illustrates a schematic structure 400 of essential functional blocks of the underlying proposed method 100. One or more digital images 402 are generated by means of known equipment for OCT measurements or OCT scans. Biometric data 404 (parametric values of the eye) are initially extracted therefrom. From the information from the extracted biometric data 404—for example the axial length of the eye—the at least one recorded digital image 402 is integrated into a graph 406 of already known recorded digital images, which are annotated with post-operative eye parameters. The integration into the graph is implemented according to the nearest neighbor principle. The graph-based neural network 408, which represents the basis for a machine learning algorithm, processes data structures which can be represented by a graph. In this way, the neural network 408 receives as input data both the biometry information determined without interruption during the method and also, at the same time, the available image information by way of the graph structure. These contain the historical scan data and the scan data of the eye for which the final location of the intraocular lens is intended to be determined—i.e., predicted. From the combination of information available thus, the neural network 408 hence predicts the desired long-term IOL position 410 in one step. Thus, further, manual intermediate steps—e.g., for manually determining the eye parameters—are dispensed with.

The neural network 408 is consequently able to extract a feature combination that has been optimized for the graph network from the images and process this in a targeted fashion taking account of the neighborhood information—i.e., taking account of adjacent scan results/image data and corresponding associated eye parameters—of a newly recorded image.

Figure 5:
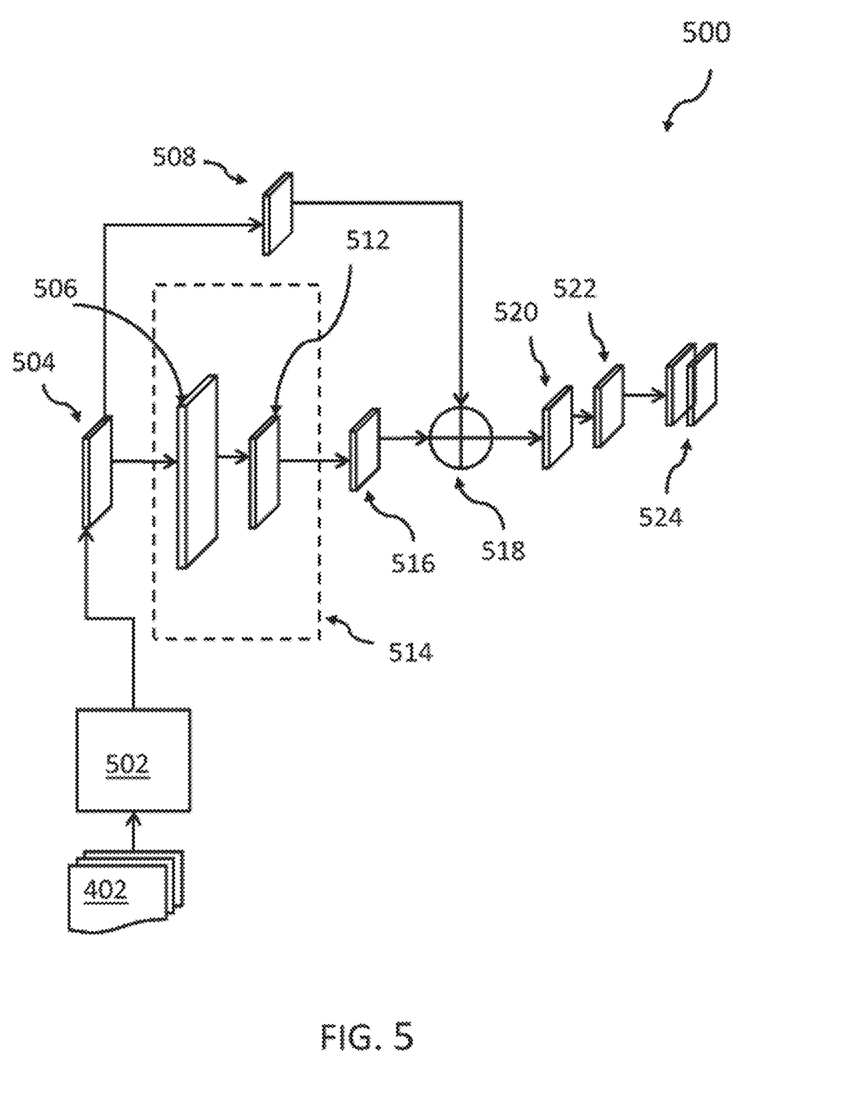
FIG. 5 illustrates example components that assist training of a machine learning system.

FIG. 5 illustrates a preferred exemplary embodiment 500 of components which assist the training of the machine learning system of the proposed method 100 and which are also used in the operative phase of the method. The recorded scan results 402, e.g., from OCT recordings of an eye, are fed to a CNN 502. By way of example, this relates to M digital recordings and N neighbors. The CNN is able to extract optimized feature information from the digital images for the following graph networks, and process said feature information taking account of the neighborhood information.

A matrix 504 of size M*N*128 can thus arise at the output of the CNN 502, which is firstly supplied to the graph processing 514 and secondly guided around the graph processing 514 by way of a matrix 508 of size M*32. The data processing components firstly consist of the graph of the nearest neighbors 506, which can be represented as a matrix of size M*N*180, which is aggregated by processing to a matrix 512 of size (M+N)*32. A matrix 516 of size M*32 is available as a result of the data processing 516 and it is merged with the matrix 508 of size M*32 by way of a concatenation function 518. This yields a matrix 520 of size M*64, which is further aggregated to a matrix 522 of size M*10. Following the application of a softmax function, there is an assignment to different prediction classes 524, which represent the desired result of the prediction of the final intraocular lens position following a healing process. In this case, the class predicted with the greatest probability is selected as final intraocular lens position. Alternatively, the final position of the IOL can also be implemented by means of a regression system as machine learning system with numerical output variables.

Figure 6:
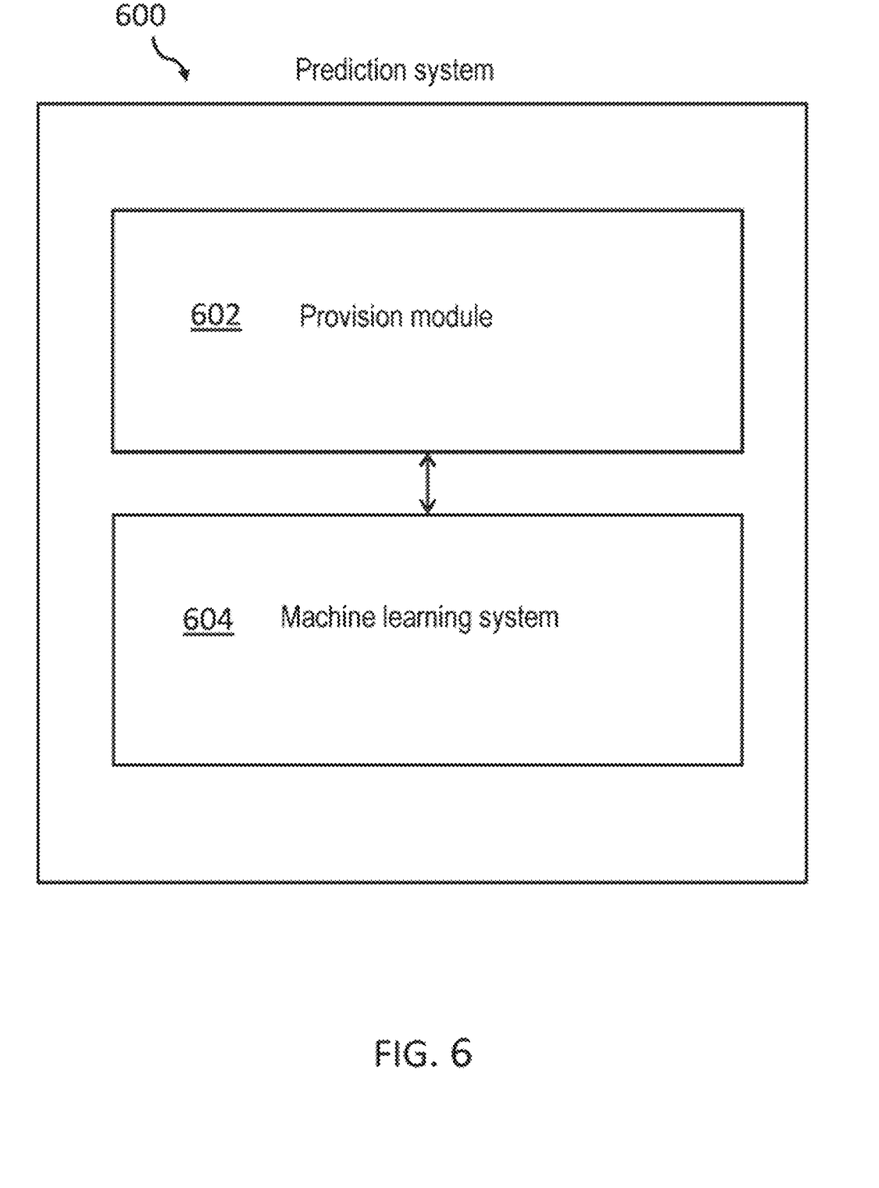
FIG. 6 illustrates a diagram of the prediction system according to the disclosure.

FIG. 6 illustrates—for the sake of completeness—essential functional blocks of the prediction system 600 for a machine learning-supported determination of position for an intraocular lens. The prediction system 600 comprises a provision module 602 adapted to provide a scan result of an eye, the scan result representing a digital image of an anatomical structure of the eye. The provision module can be realized completely by means of hardware components and can also be connected to the trained, machine learning system 604, which may also be realized completely by means of hardware, present in the prediction system 600. In this case, the machine learning system 604 is adapted to directly determine a final location of the intraocular lens to be inserted. As already described above, the scan data of the eye serve as input data for the machine learning system. The machine learning system 604 is adapted to carry out the essential steps of the components illustrated in FIG. 5.

Figure 7:
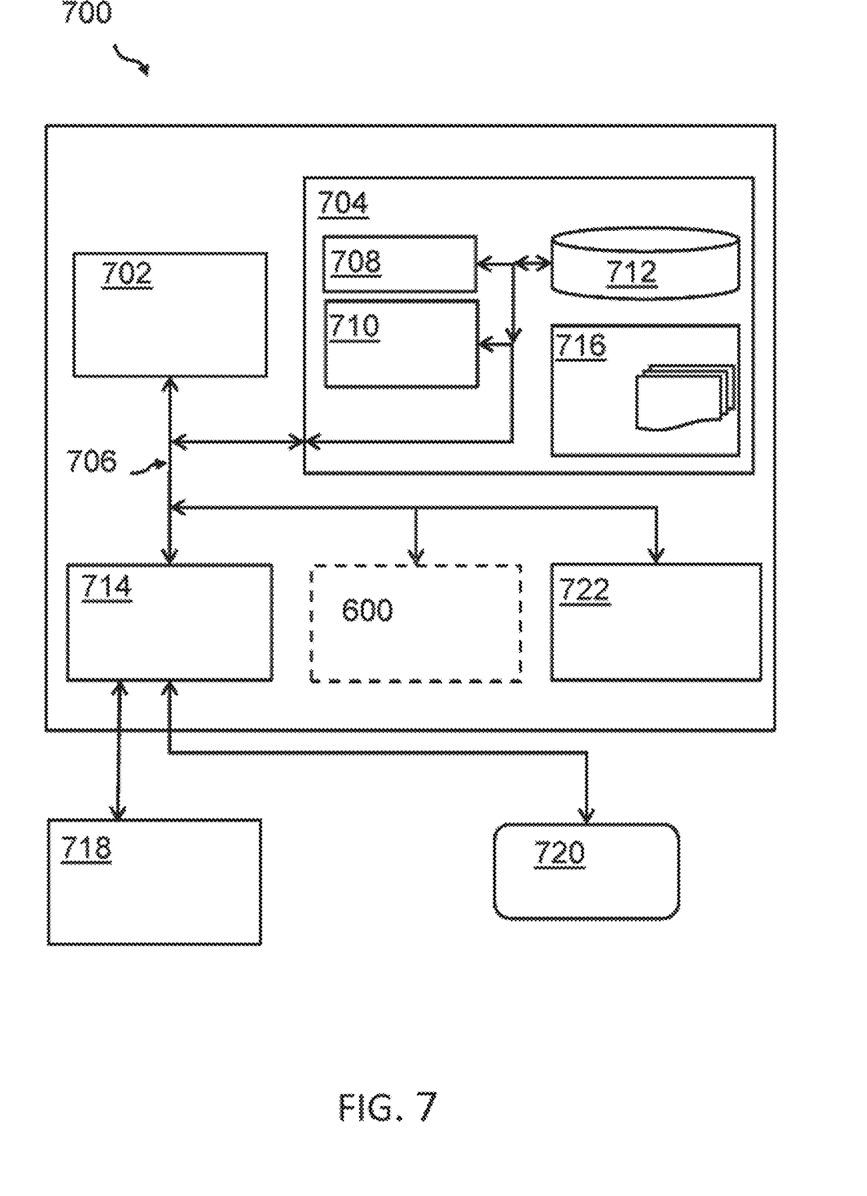
FIG. 7 depicts a diagram of a computer system which may additionally comprise the system according to FIGS. 5-6 in full or in part.

FIG. 7 illustrates a block diagram of a computer system that may have at least parts of the prediction system for a machine learning-supported determination of position for an intraocular lens. Embodiments of the concept proposed here may in principle be used together with virtually any type of computer, regardless of the platform used therein to store and/or execute program codes. FIG. 5 illustrates by way of example a computer system 700 that is suitable for executing program code according to the method proposed here but may also contain the prediction system.

The computer system 700 has a plurality of general-purpose functions. The computer system may in this case be a tablet computer, a laptop/notebook computer, another portable or mobile electronic device, a microprocessor system, a microprocessor-based system, a smartphone, a computer system with specially configured special functions or else a constituent part of a microscope system. The computer system 700 may be configured so as to execute computer system-executable instructions—such as for example program modules—that may be executed in order to implement functions of the concepts proposed here. For this purpose, the program modules may comprise routines, programs, objects, components, logic, data structures etc. in order to implement particular tasks or particular abstract data types.

The components of the computer system may comprise the following: one or more processors or processing units 702, a storage system 704 and a bus system 706 that connects various system components, including the storage system 704, to the processor 702. The computer system 700 typically has a plurality of volatile or non-volatile storage media accessible by the computer system 700. The storage system 704 may store the data and/or instructions (commands) of the storage media in volatile form—such as for example in a RAM (random access memory) 708—in order to be executed by the processor 702. These data and instructions realize one or more functions and/or steps of the concept presented here. Further components of the storage system 704 may be a permanent memory (ROM) 710 and a long-term memory 712 in which the program modules and data (reference sign 716) and also workflows may be stored.

The computer system comprises a number of dedicated devices (keyboard 718, mouse/pointing device (not illustrated), visual display unit 720, etc.) for communication purposes. These dedicated devices may also be combined in a touch-sensitive display. An I/O controller 714, provided separately, ensures a frictionless exchange of data with external devices. A network adapter 722 is available for communication via a local or global network (LAN, WAN, for example via the Internet). The network adapter may be accessed by other components of the computer system 700 via the bus system 706. It is understood in this case, although it is not illustrated, that other devices may also be connected to the computer system 700.

At least parts of the prediction system 600 (cf., FIG. 6) may also be connected to the bus system 706.

The description of the various exemplary embodiments of the present disclosure has been given for the purpose of improved understanding, but does not serve to directly restrict the inventive concept to these exemplary embodiments. A person skilled in the art will himself/herself develop further modifications and variations. The terminology used here has been selected so as to best describe the basic principles of the exemplary embodiments and to make them easily accessible to a person skilled in the art.

The principle presented here may be embodied as a system, as a method, combinations thereof and/or else as a computer program product. The computer program product may in this case comprise one (or more) computer-readable storage medium/media having computer-readable program instructions in order to cause a processor or a control system to implement various aspects of the present disclosure.

As media, electronic, magnetic, optical, electromagnetic or infrared media or semiconductor systems are used as forwarding medium; for example SSDs (solid state devices/drives as solid state memory), RAM (random access memory) and/or ROM (read-only memory), EEPROM (electrically erasable ROM) or any combination thereof. Suitable forwarding media also include propagating electromagnetic waves, electromagnetic waves in waveguides or other transmission media (for example light pulses in optical cables) or electrical signals transmitted in wires.

The computer-readable storage medium may be an embodying device that retains or stores instructions for use by an instruction executing device. The computer-readable program instructions that are described here may also be downloaded onto a corresponding computer system, for example as a (smartphone) app from a service provider via a cable-based connection or a mobile radio network.

The computer-readable program instructions for executing operations of the disclosure described here may be machine-dependent or machine-independent instructions, microcode, firmware, status-defining data or any source code or object code that is written for example in C++, Java or the like or in conventional procedural programming languages such as for example the programming language "C" or similar programming languages. The computer-readable program instructions may be executed in full by a computer system. In some exemplary embodiments, there may also be electronic circuits, such as, for example, programmable logic circuits, field-programmable gate arrays (FPGAs) or programmable logic arrays (PLAs), which execute the computer-readable program instructions by using status information of the computer-readable program instructions in order to configure or to individualize the electronic circuits according to aspects of the present disclosure.

The disclosure presented here is furthermore illustrated with reference to flowcharts and/or block diagrams of methods, devices (systems) and computer program products according to exemplary embodiments of the disclosure. It should be pointed out that practically any block of the flowcharts and/or block diagrams can be embodied as computer-readable program instructions.

The computer-readable program instructions can be made available to a general purpose computer, a special computer or a data processing system programmable in some other way, in order to produce a machine, such that the instructions that are executed by the processor or the computer or other programmable data processing devices generate means for implementing the functions or processes illustrated in the flowchart and/or block diagrams. These computer-readable program instructions may accordingly also be stored on a computer-readable storage medium.

In this sense any block in the illustrated flowchart or block diagrams can represent a module, a segment or portions of instructions representing a plurality of executable instructions for implementing the specific logic function. In some exemplary embodiments, the functions represented in the individual blocks can be implemented in a different order—optionally also in parallel.

The illustrated structures, materials, sequences and equivalents of all means and/or steps with associated functions in the claims hereinafter are intended to apply all structures, materials or sequences as expressed by the claims.

The invention claimed is:

1. A computer-implemented method for a machine learning supported pre-operative determination of a final position for an intraocular lens that is to be surgically inserted into an eye of a patient, the method comprising:
    providing a pre-operative scan result of the eye, the pre-operative scan result representing an image of an anatomical structure of the eye; and
    using a trained machine learning system to pre-operatively directly determine the final position for the intraocular lens that is going to be surgically inserted, digital data of the pre-operative scan result of the eye serving as input data for the machine learning system.

2. The method of claim 1, wherein the pre-operative scan result of the eye represents a sectional image of a plane within the eye, and a smallest angle of the plane with an ocular axis from a cornea to a retina is smaller than a specified maximum angle.

3. The method of claim 2, wherein the plane is flat or curved.

4. The method of claim 1, wherein the pre-operative scan result of the eye represents a plurality of images of the anatomical structure of the eye.

5. The method of claim 1, wherein the pre-operative scan result of the eye is generated using optical coherence tomography or ultrasound.

6. The method of claim 1, further comprising training the machine learning system using annotated scan results of eyes as input data for the machine learning system, with a model being generated in the machine learning system for rendering the final position of the intraocular lens predictable.

7. The method of claim 6, wherein parameters of the eyes associated with the annotated scan results of the eyes are used as additional input data for training the machine learning system.

8. The method of claim 1, wherein the machine learning system comprises a neural network.

9. The method of claim 1, wherein using the trained machine learning system includes integrating the pre-operative scan result of the eye into a graph of available annotated eye recordings of a same type, with the integration into the graph being undertaken on a basis of biometric data of the eye.

10. The method of claim 9, wherein the graph is constructed according to a nearest neighbor principle.

11. The method of claim 9, wherein the machine learning system comprises:
    a first stage having a first machine learning system comprising a first trained model for predicting biometric data of the eye; and
    a second stage having a second machine learning system, comprising a second trained model which uses the biometric data predicted by the first machine learning system and the graph as input data in order to predict the final position of the intraocular lens that is going to be inserted.

12. The method of claim 11, wherein parameters of the patient are also used as input data for the second machine learning system, with the parameters comprising at least one of an age, a sex, a operation location, an operating physician, an operation method, or extended pathology data.

13. The method of claim 1, wherein a type of the pre-operative scan result of the eye comprises at least one of an A scan, a B scan, volume data, en-face scan data, or dynamic eye data.

14. The method of claim 13, further comprising using wherein a recursive neural network to capture, based on the dynamic eye data, a change in the eye over time.

15. A non-transitory computer-readable storage medium storing program instructions that, when executed by one or more processors or processing units, cause the one or more processors or processing units to carry out the method of claim 1.

16. A prediction system for a machine learning supported determination of a final position for an intraocular lens that is to be surgically inserted into an eye of a patient, the prediction system comprising:
    a provision module adapted to provide a pre-operative scan result of the eye, the pre-operative scan result of the eye representing an image of an anatomical structure of the eye; and
    a trained machine learning system adapted to pre-operatively directly determine the final position for the intraocular lens that is going to be inserted, digital data of the pre-operative scan result of the eye serving as input data for the machine learning system.

17. The prediction system of claim 16, wherein the pre-operative scan result of the eye represents a sectional image of a plane within the eye, and a smallest angle of the plane with an ocular axis from a cornea to a retina being smaller than a specified maximum angle.

18. The prediction system of claim 17, wherein the plane is flat or curved.

19. The prediction system of claim 16, wherein the pre-operative scan result of the eye represents a plurality of images of the anatomical structure of the eye.

20. The prediction system of claim 16, wherein the pre-operative scan result of the eye is generated using optical coherence tomography or ultrasound.

21. The prediction system of claim 20, wherein parameters of the eyes associated with the annotated scan results of the eyes are used as additional input data for training the machine learning system.

22. The prediction system of claim 16, further comprising a training module adapted for training the machine learning system using annotated scan results of eyes as input data for the machine learning system, with a model being generated in the machine learning system for rendering the final position of the intraocular lens predictable.

23. The prediction system of claim 16, wherein the machine learning system comprises is a neural network.

24. The prediction system of claim 16, wherein using the trained machine learning system includes integrating the pre-operative scan result of the eye into a graph of available annotated eye recordings of a same type, with the integration into the graph being undertaken on a basis of biometric data of the eye.

25. The prediction system of claim 24, wherein the graph is constructed according to a nearest neighbor principle.

26. The prediction system of claim 24, wherein the machine learning system comprises:
   a first stage having a first machine learning system comprising a first trained model, by means of which biometric data of the eye are predictable; and
   a second stage having a second machine learning system comprising a second trained model which uses the biometric data predicted by the first machine learning system and the graph as input data in order to predict the final position of the intraocular lens that is going to be inserted.

27. The prediction system of claim 26, wherein parameters of the patient are also used as input data for the second machine learning system, with the parameters comprising at least one of an age, a sex, a operation location, an operating physician, an operation method, or extended pathology data.

28. The prediction system of claim 16, wherein a type of the pre-operative scan result of the eye comprises at least one of an A scan, a B scan, volume data, en-face scan data, or dynamic eye data.

29. The prediction system of claim 28, wherein a recursive neural network is used to capture, based on the dynamic eye data, a change in the eye over time.

\* \* \* \* \*